(12) United States Patent
Generale

(10) Patent No.: US 6,492,334 B1
(45) Date of Patent: Dec. 10, 2002

(54) TRI-COMPOUND ANALGESIC FOR TREATING INFLAMMATION AND PAIN

(76) Inventor: Robert James Generale, 620 Timpson St., Pelham, NY (US) 10803

( * ) Notice: Subject to any disclaimer, the term of this patent is extended or adjusted under 35 U.S.C. 154(b) by 0 days.

(21) Appl. No.: 09/648,962

(22) Filed: Aug. 26, 2000

Related U.S. Application Data

(60) Provisional application No. 60/174,016, filed on Dec. 30, 1999.

(51) Int. Cl.[7] .......................... A61K 31/70; A61K 31/16; A61K 31/14
(52) U.S. Cl. ..................... 514/23; 514/629; 514/642
(58) Field of Search ................ 514/629, 642, 514/23

(56) References Cited

U.S. PATENT DOCUMENTS

| | | | |
|---|---|---|---|
| 4,559,326 A | * 12/1985 | Crawford et al. | |
| 5,179,097 A | * 1/1993 | Angres | |
| 5,407,924 A | * 4/1995 | Siren | |
| 5,891,885 A | 4/1999 | Caruso et al. | 514/289 |
| 6,160,020 A | 12/2000 | Ohannesian | 514/629 |
| 2001/0049362 A1 | 12/2001 | Lefer et al. | 514/478 |

FOREIGN PATENT DOCUMENTS

| | | |
|---|---|---|
| WO | WO 99/47101 | 9/1999 |

OTHER PUBLICATIONS

Editors of Consumers Guide in Prescription Drugs for People over 50, Publications International, Lincolnwood, Ill., 1998, pp. 146–147, 260–263 and 266–270.

Silverman, H. And Simon, G.,in The Pill Book (5th ed.), Bantam Books, N.Y. 1992, pp. 14–16, 61–64, 412–416, 447–449, 596–599.
Reynier, 1985, Lipids 20: 145–150.
Zeisel, 1981, Ann. Rev. Nutr. 1: 95–121.
Kusisand Mookerjea, 1978, Nutrition Reviews 36:233–238.
Pardridge et al., in Nutrition and the Brain, (A. Barbeau, J.H. Growdon and R.J. Wurtman, eds.), vol. 5, Raven Press, NY, 1979, pp. 25–34.
Zeisel et al., in Nutrition and the Brain, (A. Barbeau, J.H. Growdon and R.J. Wurtman, eds.), vol. 5, Raven Press, NY, 1979, pp. 47–55.
Haubrich et al., in Nutrition and the Brain, (A. Barbeau, J.H. Growdon and R.J. Wurtman, eds.), vol. 5, Raven Press, NY, 1979, pp. 57–71.
Vergroesen in Nutrition and the Brain, (A. Barbeau, J.H. Growdon and R.J. Wurtman, eds.), vol. 5, Raven Press, NY, 1979, pp. 109–112.
McGeer et al., in Nutrition and the Brain, (A. Barbeau, J.H. Growdon and R.J. Wurtman, eds.), vol. 5, Raven Press, NY, 1979, pp. 177–194.
Salway et al., Dec. 16,1978, The Lancet, pp. 1282–1284.
Davis et al., 1975, 293:152.
Rinse, 1973, American Laboratory, pp. 23–37.
Rinse, 1973, American Laboratory, pp. 68–73.
Kapp et al., 1970, J. Neurosur. 32: 468–472.
Beams, 1946, J.A.M.A. 130:190–194.

* cited by examiner

*Primary Examiner*—William R. A. Jarvis
(74) *Attorney, Agent, or Firm*—Cheryl H. Agris

(57) ABSTRACT

A composition of an analgesic choline bitartrate, and myo-inositol and method for using same are described herein.

The composition alleviates inflammation and pain due to such causes as sciatica, injury, trauma and arthritis without the negative side effect attributable to NSAIDs.

9 Claims, No Drawings

TRI-COMPOUND ANALGESIC FOR TREATING INFLAMMATION AND PAIN

This application claims priority to provisional application No. 60/174,016, filed Dec. 30, 1999.

FIELD OF THE INVENTION

This invention relates to analgesics, specifically to a method of controlling inflammation and pain.

BACKGROUND OF THE INVENTION

All early attempts at controlling pain were eventually superseded. Shortcomings of effectiveness and negative side effects were the reasons. This has been true since the historic use of herbs. Until 1955 aspirin was the primary over the counter inflammation and pain drug. It relieves inflammation and pain, but is particularly antagonistic to the stomach. Long term use may cause bleeding and ulcers.

Acetaminophen was introduced as an analgesic without the side effects of aspirin. However, it has no effect on inflammation and it can only be used as an analgesic. Although acetaminophen does not distress the stomach, continued use will tax the liver.

Other pharmaceuticals aimed at controlling inflammation and pain are continually introduced. The broadest category is known as NSAID (Non-Steroid Anti-Inflammatory Drug).

In the case of ADVIL (the trademark name of the drug ibuprofen), both inflammation and pain can be controlled. However, ADVIL (i.e. ibuprofen) has has serious side effects, being harmful to the stomach, kidneys or liver. It also causes ringing in the ears and dizziness.

ORUDIS (the tradmark name of the drup ketaprofen), an anti-inflammatory, has the same side effects as ibuprofen. In addition, it has particular cautions for patients with ulcers or kidney disease.

ALEVE (the trademark name for the drug naproxen sodium), is an anti-inflammatory but must not be taken by patients with kidney disease or liver impairment. Also, it may cause stomach ulcers.

INDOCIN (the trademark name for the drug indomethacin), is an anti-inflammatory broadly prescribed for arthritis. However, it has no more effect on arthritis than a placebo (as reported by the American Rheumatism Association). Its side effects, among many, include liver damage and hemorrhage of the esophagus.

The newest generation of NSAIDs are COX2 inhibitors. These are widely used prescription only drugs for inflammation and pain. They are considered a more effective class of NSAID. However, as historically demonstrated, they too have a lengthy list of side effects and precautions. CELEBREX (the trademark name of the drug celecoxib) and VIOXX (the trademark drug rofecoxib) comprise the main source of COX2 inhibitors.

The following is from the patient prescription information included with a CELEBREX prescription provided by CVS, a nationwide drugstore.

"USES: This medication is a non-steroidal anti-inflammatory drug (NSAID) which relieves pain and inflammation (swelling). It is used to treat pain, swelling and stiffness due to arthritis.

SIDE EFFECTS: Stomach upset, diarrhea, gas or nausea may occur. If these effects persist or worsen, notify your doctor promptly. Unlikely but report:promptly black or bloody stools or persistent stomach pain. Very unlikely but report promptly: unusual fatigue, yellowing eyes or skin, severe headache, unexplained weight gain or change in amount of urine. In the unlikely event you have an allergic reaction to this drug, seek immediate medical attention. Symptoms of an allergic reaction include rash, itching, swelling, dizziness or trouble breathing. If you notice other effects not listed above, contact your doctor or pharmacist.

PRECAUTIONS: Tell your doctor your medical history, including any allergies to drugs such as sulfas or asprin type drugs (NSAIDs); kidney, liver or heart disease; alcohol use, high blood pressure, swelling (edema), blood disorders (anemia), serious infections, stomach problems (bleeding or ulcers), asthma, or growths in the nose (nasal polyps). This medicine may cause stomach bleeding. Daily use of alcohol, especially when combined with this medicine, may increase your risk for stomach bleeding. Check with your doctor or pharmacist for more information. This medication should be used only when clearly needed during the first 3 months of pregnancy. It is not recommended for use during the last 6 months of pregnancy. Discuss the risks and benefits with your doctor. It is not known whether this drug is excreted into breast milk. Due to the potential risk to the infant, breast feeding while using this drug is not recommended. Consult your doctor before breast feeding. Caution is advised when this drug is used in the elderly, as they may be more sensitive to the side effects of this medication.

DRUG INTERACTIONS: Tell your doctor of all prescription and non-prescription drugs you may use, especially fluconazone, lithium, "water pills" (diuretics, e.g., furosemide, hydrochlorothiazide), drugs for high blood pressure, "ACE inhibitors" (e.g. captopril, lisinopril), "corticosteroids" (e.g., prednisone-like drugs), "blood thinners" (e.g.warfarin) or NSAIDs (e.g., ibuprofen, naproxen). Check all nonprescription medicine labels carefully, since many contain pain relievers/fever reducers (NSAIDs/aspirin) which are similar to this drug. Aspirin as prescribed by your doctor for reasons such as heart attack or stroke prevention (i.e. non-arthritis doses) should be continued. Consult your pharmacist. Do not stop any medicine without doctor or pharmacist approval."

OBJECTS AND ADVANTAGES

My invention, ACI (acetaminophen, choline and inositol), controls inflammation and/or pain due to sciatica, injury, trauma and arthritis. In contrast to all NSAIDs, it has no harmful side effects to either the liver or kidneys. There are no known side effects to the stomach such as ulcers or bleeding. It will not harm the esophagus. Choline and inositolare completely natural to the body and are readily absorbed.

Choline and inositol are highly effective lipotropic agents. They are readily transported to and absorbed by the liver. Lipotropic agents produce lecithin in the liver to protect against cirrhosis and fatty liver damage. The combined action of choline and inositol is ameliorating to the antagonistic effects of acetaminophen on the liver.

SUMMARY OF THE INVENTION

A method for alleviating pain and inflammation using a composition of acetaminophen, choline and inositol, which does not provide any of the distresses to the patient as do NSAIDs. My invention is a composition of acetaminophen, choline and inositol. It is used as a non-distressing anti-inflammatory.

The main embodiment is a compound of acetaminophen, choline and inositol in a constant ratio. The dosage is variable dependent upon the severity of condition of the patient.

The preferred embodiment is the compound in capsule or tablet form. The practical dose should be considered 33.33% by weight of acetaminophen; 33.33% by weight of choline; and 33.33% by weight of inositol.

DETAILED DESCRIPTION OF THE INVENTION

Acetaminophen, an analgesic, works in the peripheral nervous system. It blocks pain impulses of trauma from going to the brain. Acetaminophen, unlike aspirin or any other conventional anti-inflammatory, does not have any effect on prostaglandins. Acetaminophen is the neutral ingredient of my invention as it relates to prostaglandins. It acts only as a broad spectrum analgesic.

Choline is a neurotransmitter and lipotropic agent. Choline along with inositol combine with methionine, an amino acid, which is omnipresent in the body. In the liver they form lecithin and are processed by enzymes into phosphytidal choline. The phosphytidal choline is transported by the blood into the brain, where it readily passes the brain blood barrier. In the brain the amino acid pyroglutamate breaks down phosphytidal choline into two neurotransmitters, specifically acetylcholine and inositol.

The brain releases the acetycholine directly into the peripheral nervous system. The nerves release the acetylcholine into all muscle receptor sites which relax all cell membranes. This makes muscles softer and more flexible, and as a result, gives the patient pain relief.

In summary, the acetylcholine is released from the brain and is transported into the peripheral nervous system. There it accelerates and amplifies the effects of acetaminophen.

Inositol is a phospholipid constituent of cell membranes. Inositol is a neurotransmitter and lipotropic agent. It regulates the functions of messenger molecules from the brain to the nervous system. It transports the movement of sodium, potassium and the electrolytes in the cells. Inositol is required for proper formation and function of cell membranes. It affects nerve transmissions and helps transport fats in the body.

The electro-chemical actions of inositol are not yet fully understood. It is speculated that inositol aids in trauma and injury by stabilizing the electrical charge in cell membranes.

Healthy cells maintain an electrical balance with a negative charge inside the cell and a positive charge on the outside. Any injury that disrupts this electrical balance will cause pain. It is believed that inositol aids in restoring electrical balance to cell membranes.

Choline and inositol are methyl donors which create sterols in the body. These sterols are precursors to prostaglandins. Prostaglandins are hormone-like substances which can be either pro-inflammatory or anti-inflammatory. Injury and trauma cause an imbalance of prostaglandins. My invention promotes a sustained release of the anti-inflammatory pro staglandins.

The invention is a new form of NSAID. It is a composition of acetaminophen, choline, and inositol (ACI).

All forms of inositol can be used in the invention. Myo-inositol is the form most bio-available to the body.

All forms of choline can be used in the invention. Phosphatidyl choline as it is found in soy should not be used because of potential allergic reactions. Choline chloride can also be used, but it has a laxative effect in high doses.

For optimum effectiveness, my invention is best utilized when choline bitartrate is combined with myo-inositol and acetaminophen. Acetaminophen is a long time used, well established analgesic.

All three ingredients-acetaminophen, choline bitartrate (or other form), and myo-inositol (or other form), act synergistically throughout the body for maximum, safe analgesic action with effective anti-inflammatory activity.

EXAMPLES

Seven subjects volunteered to participate in this study. Five were female chronic sciatica sufferers, ages 41–56, in an active state of the condition, requiring bed rest. Histories of the group were taken. Previous prescription modalities involved combinations of ANAPROX (the trademark name for the drug naproxen), EMPIRIN (the trademark name for the drug aspirin) with codeine. VALIUM (the trademark name for the drug diazepam)and muscle rubs applied with hot compresses throughout the day. Original infirmary time was from 2 to 4 weeks.

The protocol used of ACI, (my invention composition of acetaminophen, choline and inositol), consisted of 2 generic acetaminophen gel-caps of 500 mg each equaling 1 gram per dose; 4 commercial capsules of choline and inositol, each capsule contains 250 mg of choline and 250 mg of inositol equaling 1 gram of choline and 1 gram of inositol per dose. One dose, equaling 3 grams of ACI, was given every 4 hours for a total of 4 doses on the first day.

By the second day, all respondents in the sciatic group felt well enough to be out of bed and were kept on the 3 gram dose 4 times per day. By the third day, 4 of the sciatic subjects had returned to work and were told to cut their dosage to 3 doses for that day only, and then terminate the protocol. The fifth sciatic subject was able to return to work by the fourth day, and was told to remain on 3 doses for that day and then terminate the protocol. None of the subjects suffered further flare-ups of sciatica. All cases of the condition had gone into complete remission. The sixth subject, a 37 year old male, sustained an injury in judo class, involving neck, shoulder and collar bone pain. The subject was put on a 4 dose protocol the first day. Subject claimed to be able to get a sound nights sleep with little discomfort. By the evening of the second day, still on the 4 dose ACI, subject claimed most soreness was gone. By the third day subject was feeling fine, was told to cut to 3 doses for that day and then terminate the protocol.

The seventh subject was a 25 year old male with a diagnosed torn muscle. Emergency Room treatment prescribed NAPROSYN (the trademark name for the drug naproxen sodium) an NSAID, and FLEXERIL(the trademark name for the drug cyclobenzaprene) a muscle relaxant. Also prescribed was bed rest and ice packs for the next 2 to 3 days. Heat was to be used by the second day to relieve spasm. By the third day subject complained of no relief. He could not work because the prescriptions made him drowsy. Subject stopped all prescribed medication and treatment. This subject was given a protocol of 5 gram of ACI per dose, not the 3 gram ACI per dose as in the previous examples. This protocol was to be taken every hours 4 times per day. By the second day the subject was able to return to work. The protocol was terminated on the third day. All symptoms were gone.

In all examples mentioned there was no compounding of any pills and no placebos were given.

What is claimed is:

1. A composition comprising (a) acetaminophen; (b) a choline and (c) an inositol in amounts effective to control inflammation and/or pain.

2. The composition according to claim 1, wherein said choline is choline bitartrate.

3. The composition according to claim 1, wherein said inositol is myoinositol.

4. The composition according to claim 1, wherein said acetaminophen, choline and inositol are each present in the amount of about 33.33% by weight of the composition.

5. The composition according to claim 1, wherein said composition is in the form of a tablet or capsule.

6. A method for the treatment of inflammation and/or pain due to sciatica, injury, trauma, or arthritis in a person in need of such treatment comprising administering to said person an amount of the composition of claim 1 effective to treat said person.

7. The method according to claim 6, wherein said person is treated orally.

8. The method of claim 1 wherein said composition is administered orally every 4 hours up to 4 times per day.

9. A method for the treatment of inflammation and/or pain due to sciatica, injury, trauma, or arthritis in a person in need of such treatment comprising administering to said person an amount of (a) acetaminophen; (b) a choline and (c) an inositol effective to treat said person.

* * * * *

UNITED STATES PATENT AND TRADEMARK OFFICE
CERTIFICATE OF CORRECTION

PATENT NO.   : 6,492,334 B1
DATED        : December 10, 2002
INVENTOR(S)  : Robert James Generale It is certified that error appears in the above-identified patent and that said Letters Patent is hereby corrected as shown below:

<u>Title page,</u>
Item [54], replace "TRI-COMPOUND ANALGESIC FOR TREATING INFLAMMATION AND PAIN" with -- COMPOSITION AND METHOD FOR TREATING INFLAMMATION AND PAIN --.
Item [76], delete "620 Timpson St., Pelham, NY (US) 10803" and insert -- 671 Bronx River Road, Apt. 6N, Yonkers, NY 10704 --
Item [56], OTHER PUBLICATIONS, please make the following changes:
In "Editors of Consumers Guide in Prescription Drugs for People over 50, Publications International, Lincolnwood, Ill. 1998, pp. 146-147, 260-263, and 266-270", please insert after "266-270", -- 360-363 --.
In "Silverman, H. And Simon, G.,in The Pill Book (5th ed.), Bantam Books, N.Y. 1992, pp. 14 16, 61-64, 412-416, 447-449, 596-599", please insert after "596-599", -- 657-660 --.
In "Kusisand Mookerjea, 1978, Nutrition Reviews 36:233-238", please replace "Kusisand" with -- Kurksis and --.
In "Davis et al., 1975, 293:152", please insert between "Davis et al" and "1975", -- New England Journal of Medicine --.
In "Rinse, 1973, American Laboratory, pp. 68-73", please replace "1973" with -- 1978 --.

<u>Column 1,</u>
Line 31, replace "has has" with -- has had --.
Line 34, replace "tradmark name of the drup" with -- trademark name of the drug --.

<u>Column 2,</u>
Line 9, replace "asprin" with -- aspirin --.
Line 48, "replace "inositolare" with -- inositol are --.

<u>Column 3,</u>
Line 55, replace "pro staglandins" with -- prostaglandins --.

UNITED STATES PATENT AND TRADEMARK OFFICE
CERTIFICATE OF CORRECTION

PATENT NO.     : 6,492,334 B1
DATED          : December 10, 2002
INVENTOR(S)    : Robert James Generale It is certified that error appears in the above-identified patent and that said Letters Patent is hereby corrected as shown below:

Column 4,
Line 54, replace "5 gram" with -- 1.5 grams --.

Signed and Sealed this

Fifteenth Day of April, 2003

JAMES E. ROGAN
*Director of the United States Patent and Trademark Office*